United States Patent [19]

Sinigaglia

[11] Patent Number: 5,114,713
[45] Date of Patent: May 19, 1992

[54] *P. FALCIPARUM* CS-PEPTIDES AS UNIVERSAL T-CELL EPITOPE

[75] Inventor: Francesco Sinigaglia, Basel, Switzerland

[73] Assignee: Hoffmann-La Roche Inc., Nutley, N.J.

[21] Appl. No.: 353,427

[22] Filed: May 18, 1989

[30] Foreign Application Priority Data

May 24, 1988 [GB] United Kingdom ............... 8812214

[51] Int. Cl.$^5$ .................. A61K 39/00; A61K 37/02
[52] U.S. Cl. ............................... 424/88; 530/324; 530/326; 530/350
[58] Field of Search ............ 530/324, 326, 350; 424/88

[56] References Cited

U.S. PATENT DOCUMENTS

| | | | |
|---|---|---|---|
| 4,826,957 | 5/1989 | Nussenzweig et al. | 530/350 |
| 4,886,782 | 12/1989 | Good et al. | 424/88 |
| 4,915,942 | 4/1990 | Vergara et al. | 424/88 |

OTHER PUBLICATIONS

Modern Approaches to New Vaccines Including Prevention of AIDS, *Abstracts*, Sep. 9–13, 1987, p. 114.
Sinigaglia, et al., European Journal of Immunology, 18:633 (1988).
Chemical Abstracts (106:16623y) 1987.
Chemical Abstracts (107:161463w) 1987.

*Primary Examiner*—Frederick E. Waddell
*Assistant Examiner*—K. Weddington
*Attorney, Agent, or Firm*—George M. Gould; William H. Epstein; Catherine R. Roseman

[57] ABSTRACT

The present invention relates to the use of a peptide from the circumsporozoite (CS) protein of *Plasmodium falciparum* (*P. falciparum*) and the derivatives thereof as a universally recognized T-cell epitope i.e. an epitope which is recognized in association with many different human and mouse major histocompatibility complex (MHC) haplotypes e.g. in the context of the human MHC class II molecules such as DR1, DR2, DR4, DR5, DRw6, DR7 or DR9. Furthermore the present invention relates to the above-mentioned peptide per se and to immunogenic compositions comprising such a peptide or a derivative thereof. These immunogenic compositions can be used as vaccines to elicit a durable immune response against a pathogenic agent in humans and animals irrespective of the MHC haplotype of the host.

7 Claims, 7 Drawing Sheets

4

+

5b

↓ pH 7.8

6

Ac-Cys-Aca-[Ala$^{384,389}$]-*P.falc.*(380-396)-NH$_2$
|
SH                                    7b ↓ pH 3

Ac-Cys-Aca-[Ala$^{384,389}$]-*P.falc.*(380-396)-NH$_2$
|
                    8

+

[(NANP)$_3$]$_8$-K$_7$-Aca-Cys-NH$_2$
|
SH

4

↓ pH 8.7

[(NANP)$_3$]$_8$-K$_7$-Aca-Cys-NH$_2$
|
Ac-Cys-Aca-[Ala$^{384,389}$]-*P.falc.*(380-396)-NH$_2$

9

P. FALCIPARUM CS-PEPTIDES AS UNIVERSAL T-CELL EPITOPE

BACKGROUND OF THE INVENTION

The present invention relates to the use of a peptide from the circumsporozoite (CS) protein of *Plasmodium falciparum* (*P. falciparum*) and the derivatives thereof as a universally recognized T-cell epitope, i.e. an epitope which is recognized in association with many different human and mouse major histocompatibility complex (MHC) haplotypes, e.g. in the context of the human MHC class II molecules such as DR1, DR2, DR4, DR5, DRw6, DR7 or DR9. Furthermore the present invention relates to the above-mentioned peptides per se and to immunogenic compositions comprising such a peptide or a derivative thereof. These immunogenic compositions can be used as vaccines to elicit a durable immune response against a pathogenic agent in humans and animals irrespective of the MHC haplotype of the host.

It is known that chemically synthesized peptides representing selected regions of antigenic structures (B-cell epitopes) can induce antibodies which bind to the native molecules (Arnon et al., Proc. Natl. Acad. Sci. USA 68, 1450-1455 [1971]). Such peptides may be injected into a host whereby a protective antibody response is induced (for a review see Shinnick et al., Ann. Rev. Microbiol. 37, 425-446 [1983]).

However the strict genetic control of responsiveness to individual epitopes by the polymorphic class II MHC genes limits the usefulness of single epitope vaccines.

An example of an epitope which does not always elicit an immune response in a host is the repeated sequence Asn-Ala-Asn-Pro (NANP) in the CS protein of the malaria parasite *P. falciparum* (Enea et al., Science, 225, 628-630 [1984]; Dame et al., Science 225, 593-599 [1984]). The repetitive peptide was found to induce a parasite-specific immune response only in those mice carrying the $H-2^b$ haplotype. (Good et al., J. Exp. Med. 164, 655-660 [1986]; del Guidice et al., J. Immunol. 137, 2952-2955 [1986]).

Recently it has been shown that the non-immunogenic B-cell epitope of the CS protein $(NANP)_n$ can be made strongly immunogenic by conjugation to a T-cell epitope comprising amino acid residues 326 to 343 from the CS protein (Good et al., Science, 235, 1059-1062 [1987]). A peptide comprising an amino acid sequence corresponding to this T-cell epitope was covalently linked to a peptide comprising the repeat sequence $(NANP)_5$. The combined peptides elicited high titers of antibodies in B10BR and B10.A(4R) mice. Similarly Francis et al. have reported in Nature 330, 168-170 [1987] that non-responsiveness to a foot-and-mouth disease virus peptide may be overcome by combining the foot and mouse disease virus B-cell epitope with foreign helper T-cell determinants, e.g. from ovalbumin or sperm-whale myoglobin. Responses to the T-cell determinants described by Good et al. ([1987], supra) and Francis et al. (supra) were under the control of Ir genes (immune response genes). This means that only specific inbred mouse strains having the "right" MHC haplotype could recognize the T-cell epitopes used.

Since an ideal vaccine has to elicit an immune response against a pathogenic agent in all individuals it has to include T-cell epitope(s) which are recognized by all MHC haplotypes.

It has now been found that the CS.T3 peptide having the amino acid sequence

H—Asp—Ile—Glu—Lys—Lys—Ile—Ala—Lys—Met—Glu—Lys—Ala—Ser—Ser—Val—Phe—Asn—Val—Val—Asn—Ser—OH can be used as a universally recognized T-cell epitope. This means it is recognized in association with many different human and mouse MHC haplotypes e.g. in the context of the human MHC molecules DR1, DR2, DR4, DR5, DRw6, DR7 or DR9. The CS.T3 peptide corresponds to the residues 378 to 398 of the CS protein from *P. falciparum* (Dame et al., supra), but contains two alanine residues in place of the native protein's cysteine residues at Position 384 and 389. The CS.T3 peptide can therefore also be called $[Ala^{384,389}]P.falciparum$ CS(378-398).

Furthermore it has been found that derivatives of the CS.T3 peptide having minor modifications in the amino acid sequence of the peptide CS.T3 may still be used as universally recognized T-cell epitopes. Thus for example one or two amino acids may be deleted at either end of the peptide without impairing its use as a universally recognized T-cell epitope. When more than two amino acids are deleted at either end of the CS.T3 peptide the peptide may still be recognized by almost all MHC haplotypes although it has been observed that the more amino acids are deleted the more the peptide loses its capability to be recognized by different MHC haplotypes. When more than about eight amino acids are deleted at either end of the peptide it is no longer recognized as T-cell epitope by any MHC haplotype (see below).

Other modifications in the amino acid sequence of the CS.T3 peptide which may have no effect on its use as a universally recognized T-cell epitope are amino acid substitutions and additions at the C-terminus and/or the N-terminus. Thus the said CS.T3 peptide or the derivatives thereof may be part of a larger polypeptide e.g. the natural CS protein or fragments thereof or a fusion protein containing foreign peptide sequences preferably peptide sequences from another polypeptide of a malaria parasite. Furthermore the C-terminus of the CS.T3 peptide or the derivatives thereof may be amidated.

Besides modifications at the N- or the C-terminus of the peptide, modifications within the amino acid sequence of the CS.T3 peptide or its derivatives may be possible which modifications still enable the peptide or its derivatives to be used as a universally recognized T-cell epitope. These modifications may be deletions, insertions and/or amino acid substitutions. Examples of such derivatives are peptides comprising residues 378 to 398 of the CS-protein having cysteine residues at position 384 and 389 as in the native CS-protein. The general features of the modifications are that they do practically not alter the secondary or tertiary structure of the peptide (Doolittle, R. F., in "The Proteins", Vol. IV, Neurath, H. and Hill R. L., Eds., Academic Press, New York, p. 1-119. [1979]). The derivatives mentioned above must bind to the MHC class II molecules at least as well or preferably better than the CS.T3 peptide. It has been observed that derivatives in which Ile at position 383 was replaced by Leu and/or Glu at position 387 was replaced by Gly bind to both DR5 and DRw6 about 10-100 times better than the original CS.T3 sequence when the binding was measured by a competitive binding assay (Kilgus et al., Proc. Natl. Acad. Sci. U.S.A., 86, 1629-1633 [1989]).

SUMMARY OF THE INVENTION

Thus the present invention relates to the use of a polypeptide comprising the amino acid sequence

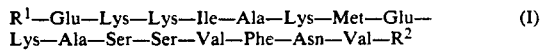

$R^1$—Glu—Lys—Lys—Ile—Ala—Lys—Met—Glu—Lys—Ala—Ser—Ser—Val—Phe—Asn—Val—$R^2$ (I)

wherein $R^1$ is H-AsP-Ile-, H-Ile- or H- and $R^2$ is -Val-Asn-Ser—OH, -Val-Asn—OH, -Val—OH or - —OH or its derivatives as a universally recognized T-cell epitope, to the polypeptide per se and to a process for the preparation of these polypeptides. The present invention relates also to immunogenic compositions comprising such a polypeptide and a polypeptide having an antigenic structure representing a B-cell epitope.

DETAILED DESCRIPTION

Figure 1:
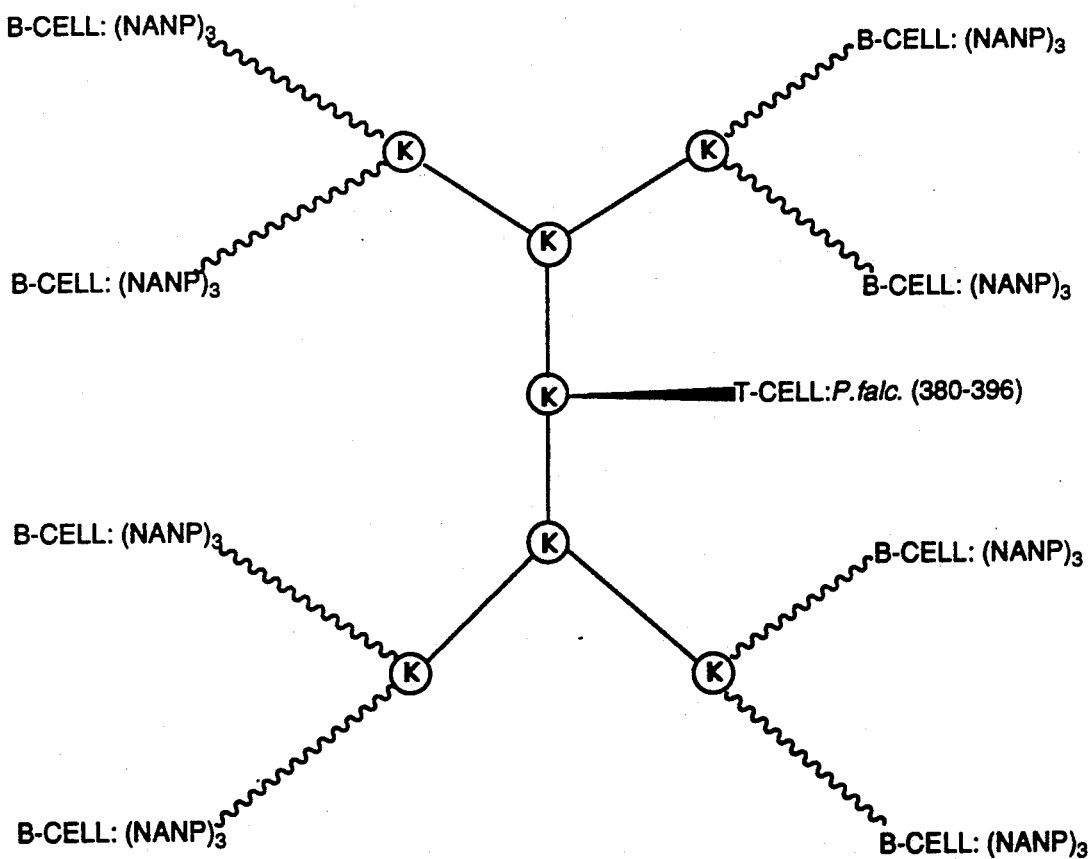

The derivatives of the polypeptides mentioned above are polypeptides having modifications in the amino acid sequence (I) such as those mentioned above which modifications do not alter the secondary or tertiary structure of the polypeptide so that these polypeptides still bind to several MHC class II molecules and thus can still be used as a universally recognized T-cell epitope.

The preferred polypeptides used in the present invention as universally recognized T-cell epitopes are the polypeptides having the following amino acid sequences

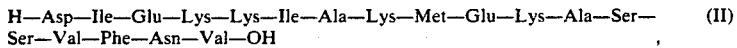
H—Asp—Ile—Glu—Lys—Lys—Ile—Ala—Lys—Met—Glu—Lys—Ala—Ser—Ser—Val—Phe—Asn—Val—OH (II)

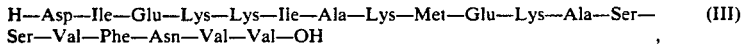
H—Asp—Ile—Glu—Lys—Lys—Ile—Ala—Lys—Met—Glu—Lys—Ala—Ser—Ser—Val—Phe—Asn—Val—Val—OH (III)

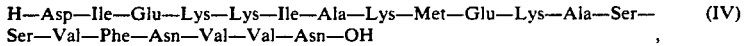
H—Asp—Ile—Glu—Lys—Lys—Ile—Ala—Lys—Met—Glu—Lys—Ala—Ser—Ser—Val—Phe—Asn—Val—Val—Asn—OH (IV)

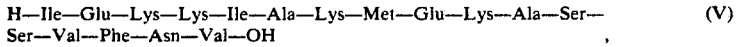
H—Ile—Glu—Lys—Lys—Ile—Ala—Lys—Met—Glu—Lys—Ala—Ser—Ser—Val—Phe—Asn—Val—OH (V)

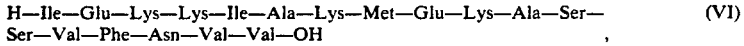
H—Ile—Glu—Lys—Lys—Ile—Ala—Lys—Met—Glu—Lys—Ala—Ser—Ser—Val—Phe—Asn—Val—Val—OH (VI)

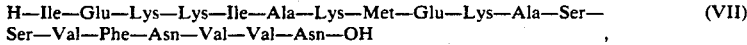
H—Ile—Glu—Lys—Lys—Ile—Ala—Lys—Met—Glu—Lys—Ala—Ser—Ser—Val—Phe—Asn—Val—Val—Asn—OH (VII)

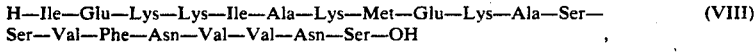
H—Ile—Glu—Lys—Lys—Ile—Ala—Lys—Met—Glu—Lys—Ala—Ser—Ser—Val—Phe—Asn—Val—Val—Asn—Ser—OH (VIII)

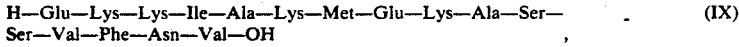
H—Glu—Lys—Lys—Ile—Ala—Lys—Met—Glu—Lys—Ala—Ser—Ser—Val—Phe—Asn—Val—OH (IX)

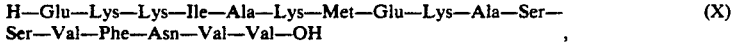
H—Glu—Lys—Lys—Ile—Ala—Lys—Met—Glu—Lys—Ala—Ser—Ser—Val—Phe—Asn—Val—Val—OH (X)

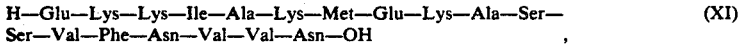
H—Glu—Lys—Lys—Ile—Ala—Lys—Met—Glu—Lys—Ala—Ser—Ser—Val—Phe—Asn—Val—Val—Asn—OH (XI)

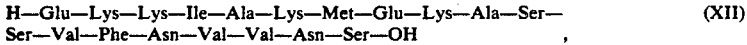
H—Glu—Lys—Lys—Ile—Ala—Lys—Met—Glu—Lys—Ala—Ser—Ser—Val—Phe—Asn—Val—Val—Asn—Ser—OH (XII)

or

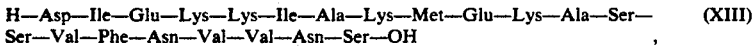
H—Asp—Ile—Glu—Lys—Lys—Ile—Ala—Lys—Met—Glu—Lys—Ala—Ser—Ser—Val—Phe—Asn—Val—Val—Asn—Ser—OH (XIII)

or derivatives of the polypeptides comprising the amino acid sequences (II) to (XIII).

The most preferred polypeptide used in the present invention as a universally recognized T-cell epitope is the polypeptide having the amino acid sequence XIII which polypeptide is identical with the CS.T3 peptide mentioned above.

As outlined above the combination of a T-cell epitope and a B-cell epitope is the functional unit which is capable of inducing a T-helper cell dependent immune response. Therefore the T-cell epitope mentioned above has to be associated with a B-cell epitope in order to elicit an immune response in a host. The B-cell epitope may be any peptide, hapten or carbohydrate representing a selected region of an antigenic structure. Such an antigenic structure may be part of a polypeptide which polypeptide may be glycosylated or not. The said polypeptide may be a surface protein of a pathogenic agent e.g. a disease-causing bacterium, virus, fungus or parasite. Examples of such pathogenic agents are described in Davis et al., "Microbiology", 3rd ed., Harper International Edition.

The peptide used as a universally recognized T-cell epitope of the present invention can be covalently coupled to any peptide, hapten or carbohydrate representing a B-cell epitope. The coupling may be either directly by the formation of a peptide or an ester bond between free carboxyl, amino or hydroxyl groups on the peptide used as a universally recognized T-cell epitope and corresponding groups on the peptide, hapten or carbohydrate representing a B-cell epitope or indirectly via a conventional bifunctional linking group. Examples of conventional bifunctional linking reagents used for the formation of such linking groups are sulfosuccinimidyl 4-(p-maleimidophenyl)butyrate (sulfo-SMPB), sulfosuccinimidyl(4-iodoacetyl)aminobenzoate (sulfo-SIAB). N-succinimidyl(4-iodoacetyl)aminobenzoate (SIAB), 2-iminothiolane.HCl (Traut's reagent), dimethyl pimelimidate.2HCl (DMP), succinimidyl 4-(p-maleimidophenyl)butyrate (SMPB), N-succinimidyl 3-(2-pyridyldithio)propionate (SPDP), bis-maleimidohexane (BMH) and m-maleimidobenzoyl-N-hydroxysuccinimide ester (MBS). These and further bifunctional linking reagents are commercially available from Pierce Chemical Company, Rockford, Ill., U.S.A. Alternatively $C_{2-7}$-dialkanals such as glutaraldehyde (Avrameas, Immunochem. 6, 43-52 [1969]) may be used.

Furthermore the B-cell and the T-cell epitope may be part of a multiple antigenic peptide (MAP). Such MAP's may be prepared as described by Posnett et al., J. Biol. Chem. 263, 1719-1725 [1988]. An example of a MAP is the multiple antigenic peptide system (MAPS) B-cell epitope [(NANP)$_3$]$_8$-Lys$_7$-Aca-Cys-NH$_2$ comprising multimers of the repeat sequence (NANP) present in the CS protein of *Plasmodium falciparum* (International Patent Application No. PCT/US85/01416, Publication No. WO 86/00911). This MAPS can be synthesized by a solid phase procedure. It has been found in two separate immunization studies that this MAPS elicits comparable antibody titers to that observed for the [Ac-Cys(NANP)$_3$]$_{25}$ B-cell epitope conjugated to the tetanus toxoid (Herrington et al., Nature 328, 257-259 [1987]). This observation was particularly important since the said MAPS B-cell epitope is a well defined homogeneous peptide which permits exact dosing and does not require conjugation to a carrier protein (e.g. tetanus toxoid) to elicit high antibody titers. Therefore the MAPS B-cell epitope approach may overcome the problems associated with the peptide vaccines conjugated to protein carriers which include (a) microheterogeneity of peptide-protein conjugation and (b) antibody response to tetanus toxoid itself which may interfere with the immune response to the synthetic peptide portion of the conjugate (Herrington et al., supra).

Thus, as a further improvement in the attempt to develop an ideal vaccine with long-term immunity at both the T-cell and B-cell level, the polypeptides having the amino acid sequence I or derivatives thereof may be combined with the above-mentioned MAPS B-cell epitope. For example the polypeptide having the amino acid sequence XIII (see Example, compound 5a) or the polypeptide having the amino acid sequence X (see Example, compound 7a) may be combined with the MAPS B-cell epitope [(NANP)$_3$]$_8$-Lys$_7$-Aca-Cys-NH$_2$. A schematic representation of the latter peptide/peptide vaccine is shown in FIG. 1. In the peptide/peptide vaccines mentioned above the peptide representing the T-cell epitope is covalently linked to the peptide representing the B-cell epitope. However there is no need that the peptide representing the T-cell epitope is covalently linked to the peptide representing the B-cell epitope, only that the peptides be associated in such a way as to lead to joint presentation to cells of the immune system.

The peptides representing the B-cell and/or the T-cell epitope can be prepared by conventional peptide synthetic methods, either in solution or, preferably by the solid phase method of Merrifield (J. Am. Chem. Soc. 85, 2149-2154 [1963]) or any other equivalent methods known in the art.

Solid phase synthesis is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin, a methylbenzhydrylamine (MBHA) resin or a benzyloxybenzyl alcohol resin. These resins are available commercially, and their preparation and use are well known.

General methods for protecting and removing protecting groups from amino acids which can be used in this invention are described in "The Peptides: Analysis, Synthesis, Biology", Vol. 2, (E. Gross and J. Meienhofer, Eds., Academic Press., New York, P. 1-284 [1979]) and by Atherton et al., in "The peptides: Analysis, Synthesis, Biology", Vol. 9, (S. Udenfried and J. Meienhofer, Eds., Academic Press, New York [1987]). Protecting groups include, e.g., the 9-fluorenylmethyloxycarbonyl (Fmoc), tert.-butyloxycarbonyl (Boc), benzyl (Bzl), t-butyl (But), 2-chlorobenzyloxycarbonyl (2Cl-Z), dichlorobenzyl (Dcb) and 3,4-dimethylbenzyl (Dmb) groups.

After removal of the α-amino protecting group from the initial (C-terminal) amino acid, the remaining protected amino acids are coupled step-wise in the desired order. The entire peptide may be synthesized in this way. Alternatively, small polypeptides may be constructed which are later joined, to give the final peptide product. Appropriate coupling procedures are known in the art, with the procedure of Dourtoglou et al. (Synthesis 1984, p. 572-574) using 3-dicyclohexylcarbodiimide/1-hydroxybenzotriazole (DCC/HOBt) or O-benzotriazolyl-N,N,N',N'-tetramethyluronium hexafluorophosphate (HBTU) being particularly suitable.

Each protected amino acid or peptide is introduced into the solid phase reactor in excess, and the coupling may be carried out in a medium of dimethylformamide (DMF) or methylene chloride (CH$_2$Cl$_2$), or a mixture thereof. In cases where incomplete coupling occurs, the coupling procedure is repeated before removal of the Nα-amino protecting group prior to the coupling of the next amino acid. The success of the coupling reaction at each stage of synthesis may be monitored. A preferred method of monitoring the synthesis is by the ninhydrin reaction. The coupling reactions and washing steps can be performed using automated instrumentation.

Cleavage of the peptide from the resin can be effected using procedures well known in peptide chemistry. For example, reaction with hydrogen fluoride (HF) in the presence of p-cresol and dimethylsulfide at 0° C. for 1 hour may be followed by a second reaction with hydrogen fluoride in the presence of p-cresol for 2 hours at 0° C. or with trifluoroacetic acid/methylene chloride/anisole. Cleavage of peptides from chloromethylated or P-benzyloxybenzyl alcohol resin supports produces finished peptides having carboxyl groups at the C-termini. Cleavage of peptides from benzhydrylamine or methylbenzhydrylamine resins produces peptides having C-terminal amide groups.

Alternatively the peptide used as a universally recognized T-cell epitope or the combined peptide containing in addition the peptide representing the B-cell epitope can be prepared using methods of the recombinant DNA technology. The methods for preparing such peptides by recombinant DNA technology are well known in the art. A DNA fragment coding for said peptide may be prepared according to procedures well known in the art, e.g. by the phosphotriester method (Narang et al., Meth. Enzymol. 68, 90-108 [1979]) or the phosphodiester method (Brown et al., Meth. Enzymol. 68, 109-151 [1979] and cloned into an expression vector as described by Maniatis et al. in "Molecular Cloning -

A Laboratory Manual", Cold Spring Harbor Laboratory [1982].

The peptides used in the present invention can be purified by known methods, such as differential centrifugation, precipitation with ammonium sulfate, dialysis to remove salts (under normal or reduced pressure), preparative iso-electric focusing, preparative gel electrophoresis or various chromatographical methods, e.g., gel filtration, high performance liquid chromatography (HPLC), ion exchange chromatography, reverse phase chromatography or affinity chromatography.

The immunogenic compositions comprising a peptide representing a universal T-cell epitope according to the present invention and a peptide representing a B-cell epitope may comprise additionally a pharmaceutically acceptable adjuvant. The said immunogenic compositions can be used as vaccines to elicit the formation of antibodies specific for a pathogenic agent expressing the B-cell epitope mentioned above. The term "Pharmaceutically acceptable adjuvant" can mean either the standard compositions which are suitable for human administration or the typical adjuvants and excipients (e.g. serum albumin or plasma preparations) employed in animal vaccinations. Suitable adjuvants for the vaccination of animals include but are not limited to Freund's complete or incomplete adjuvant (not suitable for human or livestock use). Adjuvant 65 (containing peanut oil, mannide monooleate and aluminum monostearate), mineral gels such as aluminum hydroxide, aluminum phosphate and alum. surfactants such as hexadecylamine, octadecylamine, lysolecithin, dimethyldioctyldecylammonium bromide, N,N-dioctadecyl-N',N'-bis(2-hydroxyethyl)Propanediamine, methoxyhexydecylglycerol and pluronic polyols, polyanions such as pyran, dextran sulfate, polyIC, polyacrylic acid and carbopol, peptides and amino acids such as muramyl dipeptide, dimethylglycine, tuftsin and oil emulsions. The polypeptide of the present invention can also be administered following incorporation into liposomes or other micro-carriers, or after conjugation to polysaccharides, other proteins or other polymers or in combination with Quil-A to form "Iscoms" (immunostimulating complexes) (Allison et al., J. Immunol. Meth. 95, 157-168 [1986]; Morein et al., Nature 308, 457-460 [1984]). In addition, genetically engineered microorganisms such as vaccinia or salmonella which are capable of expressing genes encoding a polypeptide representing a universal T-cell epitope can be used as vaccine delivery systems (Mackett. Immunol. Letters 16, 243-248 [1987]).

The immunogenic compositions are prepared by combining a peptide representing a universal T-cell epitope according to the present invention with a peptide representing a B-cell epitope and if necessary with a pharmaceutically acceptable adjuvant. Preferably the immunogenic compositions are in the form of a unit dose. The amount of active compounds administered as a vaccination or as a medicament at one time, or over a period of time, will depend on the subject being treated, the manner and form of administration, and the judgement of the treating physician. However, an effective dose may be in the range of from about 1 ng to about 1 mg of the composition of this invention, preferably about 100 µg to about 500 µg; it being recognised that lower and higher doses may also be useful. The immunogenic composition may be in a variety of forms. These include, for example solid, semi-solid and liquid dosage forms. The unit dose is preferably packed in 1 ml vials containing the immunogenic composition in form of a suspension in sterile 0.9%(w/v) NaCl solution. The most preferred immunogenic composition comprises 0.4 mg/ml protein (T- and B-cell epitope peptides) adsorbed to 850 µg Al(OH)$_3$/ml and 100 µg/ml Merthiolate TM (Eli Lilly). The vial is preferably packed in a container together with written instructions informing on the correct use of the immunogenic composition. The present invention relates also to such a unit dose of the immunogenic composition packed in a container, most preferably together with the appropriate instructions. Furthermore the present invention relates to a process for the preparation of said immunogenic compositions or of a unit dose thereof as well as to a method for the immunization of a human or animal using such an immunogenic composition.

The form and the route of administration of the immunogenic composition as well as frequency of injections are all factors which can be optimized using ordinary skill in the art. Typically, the initial vaccination with an immunologically effective amount of the vaccine is followed some weeks later by one or more "booster" vaccinations, the net effect of which is the production of high titers of antibodies against the particular pathogenic agent.

Having now generally described this invention, the same may be more readily understood by reference to the following example in connection with the accompanying FIGS. 1 to 6.

FIG. 1 Schematic representation of the peptide/peptide vaccine comprising the MAPS B-cell epitope [(NANP)$_3$]$_8$-Lys$_7$-Aca-Cys—NH$_2$ and the T-cell epitope Ac-Cys-Aca[Ala$^{384,389}$]-P.falciparum CS(380-396)—NH$_2$. N,A,P,K stand for asparagine, alanine, proline and lysine, respectively.

Figure 2A:
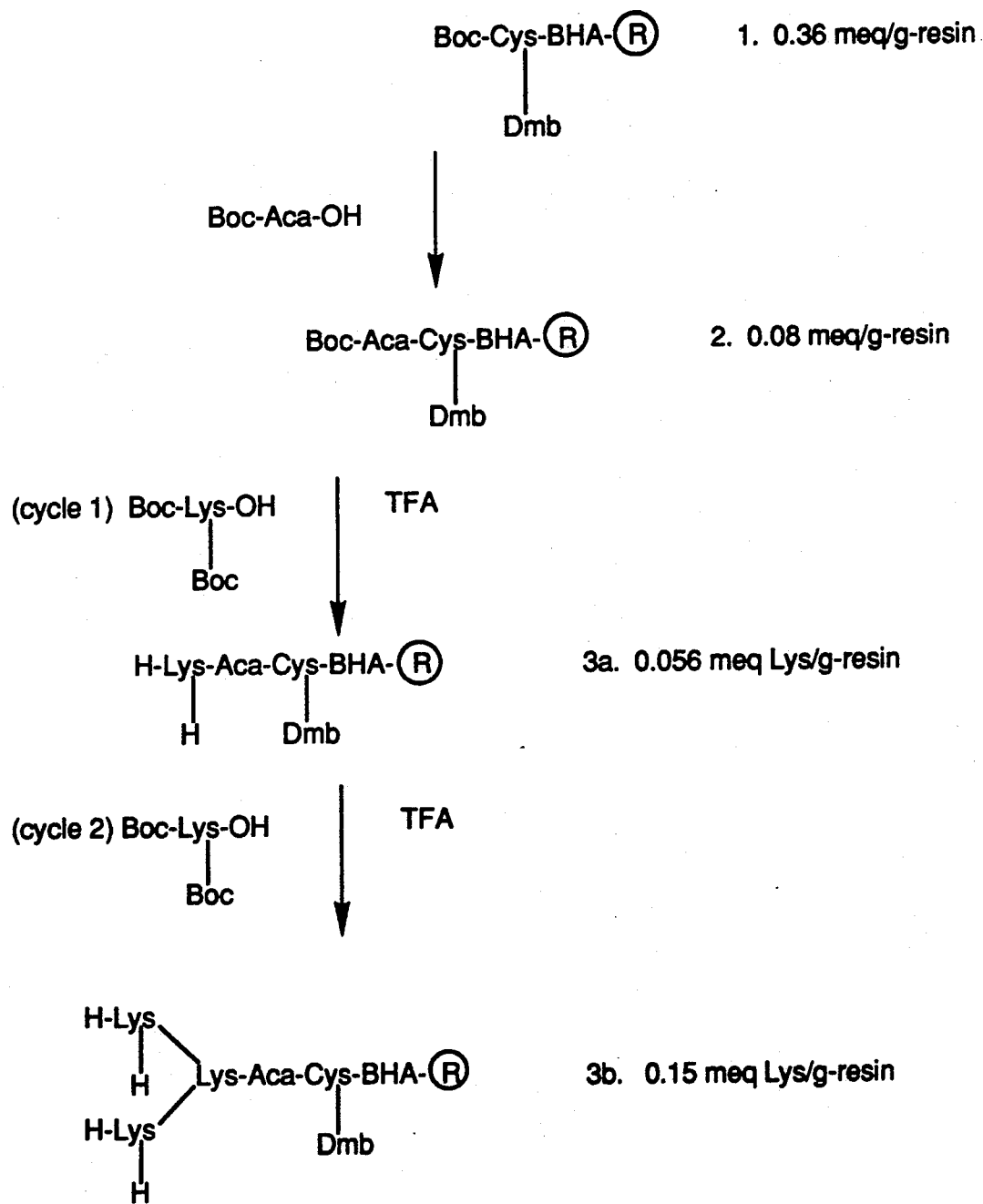
Figure 2B:
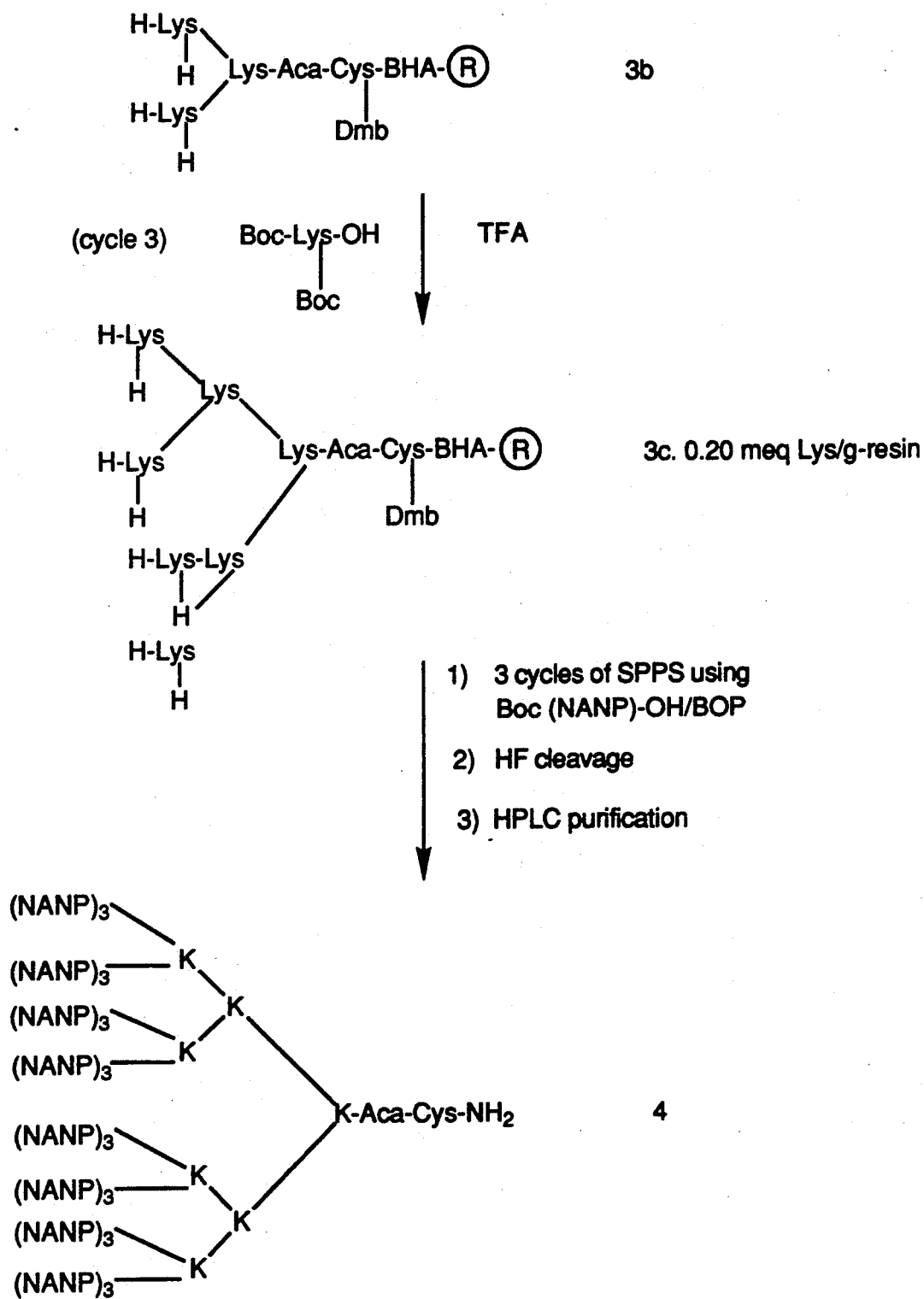

FIG. 2A,B Schematic representation of the solid phase peptide synthesis (SPPS) of the MAPS B-cell epitope [(NANP)$_3$]$_8$-Lys$_7$-Aca-Cys—NH$_2$.

Figure 3:
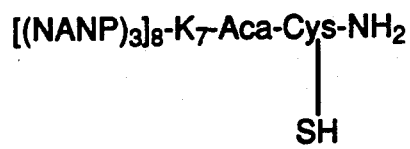
Figure 3:
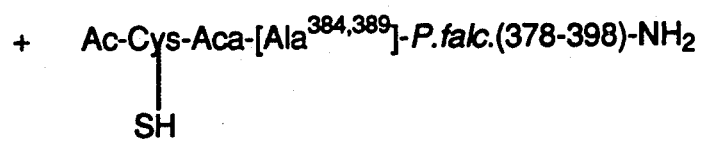
Figure 3:
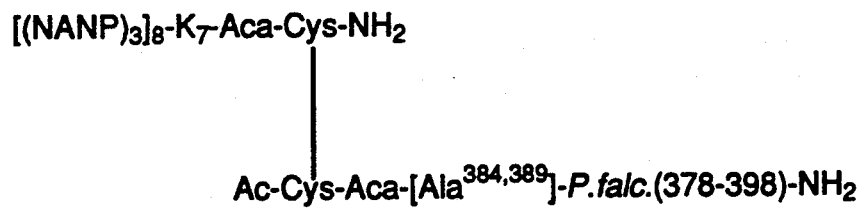

FIG. 3 Schematic representation of the covalent linking of the MAPS B-cell epitope [(NANP)$_3$]$_8$-Lys$_7$-Aca-Cys—NH$_2$ with the universal T-cell epitope Ac-Cys-Aca-[Ala$^{384,389}$]-P.falciparum CS(378-398)—NH$_2$.

Figure 4:
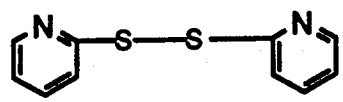
Figure 4:
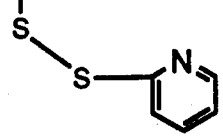

FIG. 4 Schematic representation of the covalent linking of the MAPS B-cell epitope [(NANP)$_3$]$_8$-Lys$_7$-Aca-Cys—NH$_2$ with the universal T-cell epitope Ac -Cys-Aca-[Ala$^{384,389}$]-P.falciparum CS(380-396)—NH$_2$ via 2,2'-dipyridyl disulfide.

Figure 5:
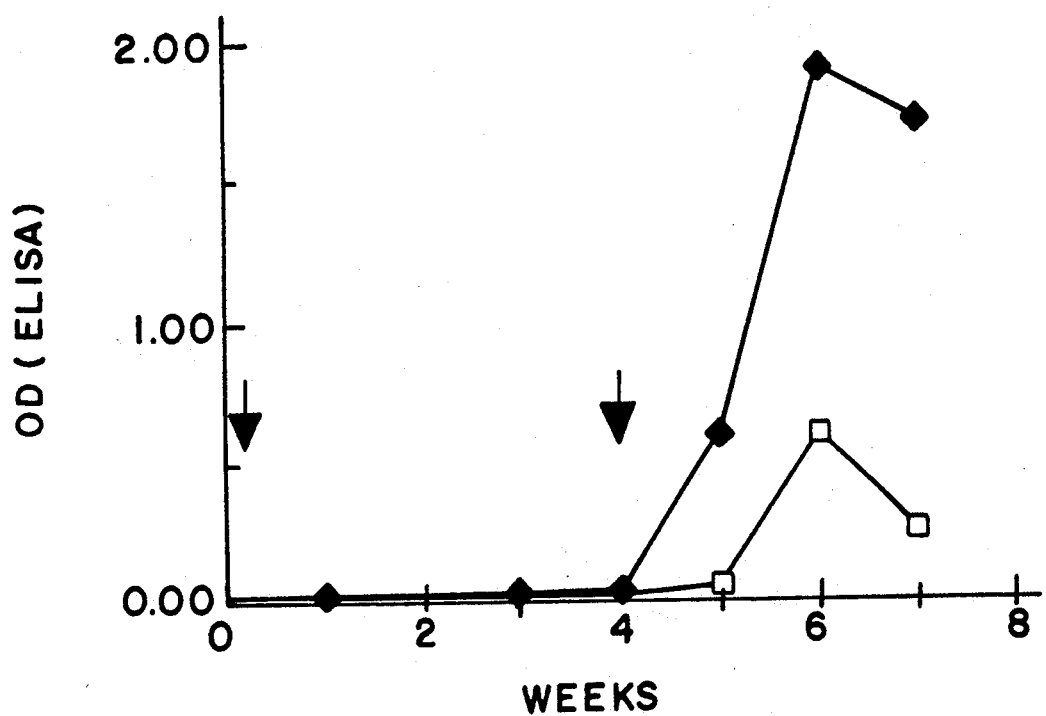

FIG. 5 Enzyme-linked immunoadsorbent assay for the presence of anti-(NANP)$_{50}$ antibody in plasma of BALB/c mice immunized with (NANP)$_3$-CS.T3(□—□)or with the universal T-cell epitope Ac-Cys-Aca-[Ala$^{384,389}$]-P.falciparum CS(378-398)—NH$_2$ covalently linked to the MAPS B-cell epitope [(NANP)$_3$]$_8$-Lys$_7$-Aca-Cys—NH$_2$(♦—♦).

Figure 6:
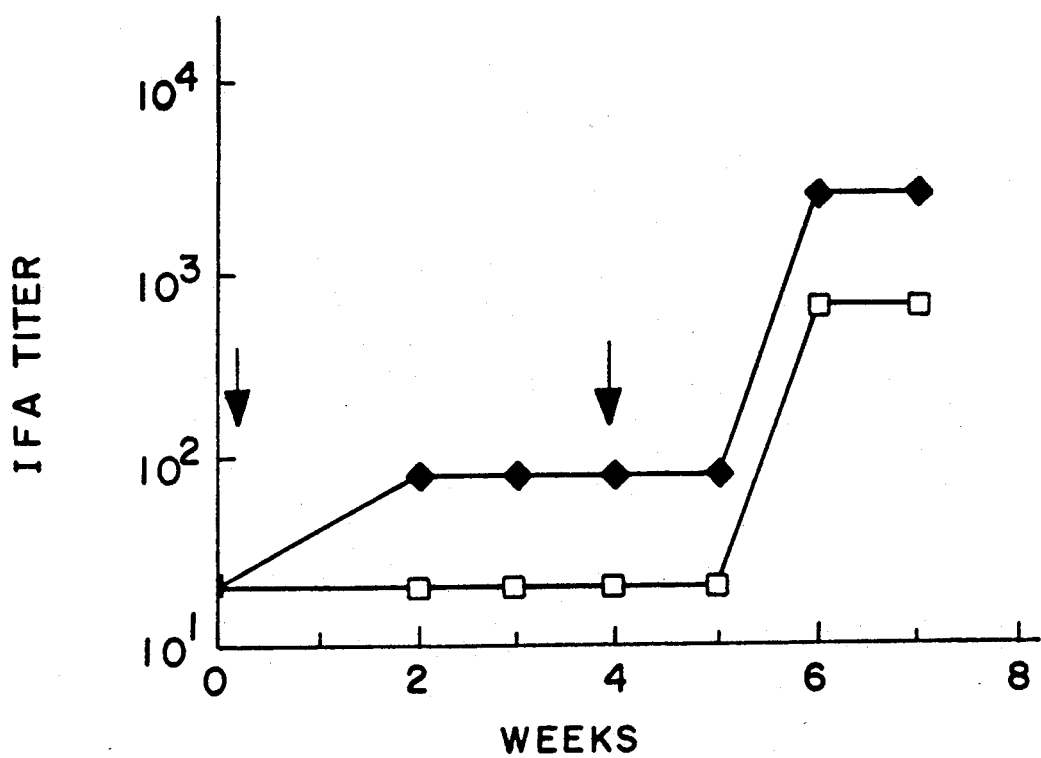

FIG. 6 Immunofluorescence assay (IFA) for the presence of anti-(NANP)$_{50}$ antibody in plasma of BALB/c mice immunized with (NANP)$_3$-CS.T3(□—□)or with the universal T-cell epitope Ac-Cys-Aca-[Ala$^{384,389}$]-P.falciparum CS(378-398)—NH$_2$ covalently linked to the MAPS-B-cell epitope [(NANP)$_3$]$_8$-Lys$_7$-Aca-Cys—NH$_2$(♦—♦).

It should be understood that the following example is for illustrative purposes only and should not be construed as limiting this invention in any way to the specific embodiment recited therein. The abbreviations used are in accordance with those generally used in peptide chemistry (see "The Peptides", Vol. 2, S. Udenfriend and J. Meienhofer, Eds.,

EXAMPLE

Synthesis and purification of the CS.T3 peptide

Peptide CS.T3 was synthesized by the solid-phase technique using base-labile N-fluorenylmethoxylcarbonyl-amino acids, t-butyl based side chain protecting groups and a p-benzyloxybenzylalcohol polystyrene resin as described by Atherton et al. in "The Peptides: Analysis, Synthesis, Biology", Vol. 9, (S. Udenfriend and J. Meienhofer, Eds., Academic Press, New York [1987]). The initial synthesis was started with the Fmoc-Ser(But) —O—CH$_2$C$_6$H$_4$O—CH$_2$C$_6$H$_4$-resin in a manual shaker. The protocol for a typical synthetic cycle was as follows:

| Step | Reagent | Time |
|---|---|---|
| 1 | N,N-dimethylformamide (DMF) | 2 × 1 min. |
| 2 | 20% piperidine/DMF | 1 × 7 min. |
| 3 | DMF | 5 × 1 min. |
| 4 | 2,5 eq. Fmoc-amino acid/DMF + 2,5 eq. HBTU + 2,5 eq. N-ethyldiisopropylamine | 1 × 90 min. |
| 5 | DMF | 3 × 1 min. |
| 6 | isopropyl alcohol (i-PrOH) | 2 × 1 min. |

The resulting protected peptide resin H-AsP(OBut)-Ile -Glu(OBut)-Lys(Boc)-Lys(Boc) -Ile-Ala-Lys(Boc)-Met-Glu(OBut) -Lys(Boc)-Ala-Ser(But) -Ser(But)-Val-Phe-Asn-Val-Val-Asn -Ser(But) —O—CH$_2$C$_6$H$_4$OCH$_2$C$_6$H$_4$-resin was treated with trifluoroacetic acid-methylene chloride-anisol (49:49:2) to yield the free peptide. The peptide was purified by high-performance liquid chromatography (HPLC) using a Lichrosorb RP18 (10μ) column (Merck, Darmstadt, FRG) in a 0,1% trifluoroacetic acid-ethanol gradient system.

The triatriakontapeptide (NANP)$_3$-CS.T3 was synthesized by a combination of the classical solution technique and solid phase peptide synthesis. The protected tetrapeptide Fmoc-Asn-Ala-Asn-Pro-OH was synthesized according to the following scheme:

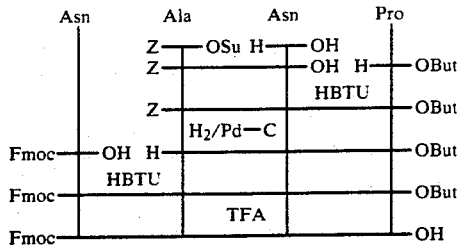

Three repeated couplings of the N$^\alpha$-protected tetrapeptide via the HBTU procedure to the N$^\alpha$-unprotected above described peptide resin yielded the protected triatriakontapeptide resin. Treatment with trifluoroacetic acid (TFA)/ methylene chloride/anisole liberated the free peptide. Purification was achieved by HPLC in the above mentioned gradient system.

The peptide was homogeneous by analytical HPLC and showed the expected amino acid composition after acid hydrolysis.

Restriction specificity of CS.T3-specific T-cell clones

Peripheral blood mononuclear cells (PBMC) from 8 volunteers (European blood donors MG, DP, JK, BR, BH, AH, SD and PE with no history of malaria infection) were HLA typed using a standard National Institutes of Health (Bethesda, Maryland, U.S.A.) complement-mediated microtoxicity assay (Amos, D. B., "Cytotoxicity testing", in NIHD Manual of Tissue Typing Techniques, NIH Publication 80–545 [1979], U.S. Department of Health, Education and Welfare, Atlanta, Ga., U.S.A.). The cells were stimulated with peptide CS.T3 (10 μg/ml), expanded in IL-2-containing medium and cloned as previously described (Sinigaglia et al., Eur. J. Immunol. 17, 187–192 [1987]). To test antigen reactivity and restriction specificity of the clones in a proliferative assay, cloned T-cells (2×10$^4$) were cocultured in triplicate with 10$^4$ irradiated autologous, or DR homozygous EBV transformed B-cells (Sinigaglia et al., EMBO J. 4, 3819–3822 [1985]) in 0,2 ml complete medium with or without the antigen CS.T3 (10 μg/ml). 3H-thymidine incorporation was measured 72 h later. Results, expressed as mean values of counts per minute (cpm) of representative clones are shown in Table 1.

TABLE 1

Proliferation of T-cell clones, measured as $^3$H-thymidine uptake (cpm), in presence of peptide CS.T3 and various antigen-presenting cells (APC).

| DR-type of APC | T-cell clone | | | | | | |
|---|---|---|---|---|---|---|---|
| | DP52 | MG30 | DP11 | SD13 | BR82 | SD22 | MG15 |
| AUTOLOGOUS | 14616 | 10241 | 10387 | 29031 | 22355 | 29889 | 10594 |
| AUTOLOGOUS + anti DR | 1021 | 307 | 463 | 1522 | 1257 | 729 | 1100 |
| DR1 (EDR) | 38226 | 441 | 913 | 810 | 1100 | 404 | 977 |
| DR2 (NOL) | 514 | 34388 | 754 | 1024 | 941 | 585 | 609 |
| DR4 (BSM) | 724 | 394 | 29210 | 991 | 882 | 354 | 570 |
| DR5 (ATH) | 301 | 474 | 925 | 50400 | 1152 | 1610 | 796 |
| DRw6 (APD) | 845 | 765 | 739 | 784 | 18109 | 798 | 697 |
| DR7 (EKR) | 305 | 450 | 434 | 627 | 1209 | 30113 | 358 |

TABLE 1-continued

Proliferation of T-cell clones, measured as $^3$H-thymidine uptake (cpm), in presence of peptide CS.T3 and various antigen-presenting cells (APC).

| DR-type of APC | T-cell clone | | | | | | |
|---|---|---|---|---|---|---|---|
| | DP52 | MG30 | DP11 | SD13 | BR82 | SD22 | MG15 |
| DR9 (DKB) | 523 | 614 | 638 | 662 | 508 | 365 | <u>40998</u> | anti DR: = monoclonal antibody E.31

As shown in table 1 the T-cell clones respond equally well to the CS.T3 antigen when presented on the autologous EBV-B cell or on the DR-homozygous EBV-B line carrying one of the donor's DR specificities. Thus at least 7 different DR molecules are able to associate with the CS.T3 peptide for presentation. The anti-DR monoclonal antibody E.31 (Trucco et al., Immunol. Rev. 47, 219-242 [1979]) was added to cultures as a 1/100 dilution of ascites fluid.

From donor MG (HLA type DR2,9) 12 CS.T3-specific clones were obtained, 8 were restricted to DR2 and 4 to DR9; from DP (DR1,4) 11 CS.T3-specific clones were analyzed, 3 were DR1-restricted and 8 DR4-restricted; from JK (DRwll(5),7) 9 CS.T3-specific clones were analyzed which were all restricted to DR5; from BR (DR4,w6) 10 CS.T3-specific clones were tested, half of them were DR4 and half DRw6-restricted; from BH (DR 1,3) 16 antigen-specific clones were obtained, all of them restricted to DR1; from SD (DR5,7) 17 clones were tested, 4 of them restricted to DR5 and 13 to DR7, and finally 13 CS.T3-specific clones were obtained from PE (DR5,w6), 13 were DR5-restricted and none was restricted to DRw6. All the CS.T3-specific clones obtained were CD4+, CD8-, indicating that they were T-helper cells (T$_H$) (Engleman et al., J. Exp. Med. 153, 193-198 [1981]).

Altogether 298 anti-CS.T3 clones were derived from the stimulated PBMC by limiting dilution. All 298 T-cell clones were specific for CS.T3 and did not proliferate in presence of a control peptide derived from the CS protein of P. falciparum (amino acid residues 325-342 of the CS protein). The MHC restriction pattern of each CS.T3-specific T-cell clone was evaluated by examining the effects of anti-MHC class II monoclonal antibodies (mAbs) on T-cell proliferative responses. The proliferation of 187 clones tested was inhibited by monoclonal antibody E.31 which recognizes a monomorphic DR determinant (Table 1). Neither anti-DP (Watson et al., Nature 304, 358-361 [1983]) nor anti-DQ (Ziegler et al., Nature 279, 243-244 [1979]) antibodies were effective. These results demonstrate that the DR molecule is the restriction element for the CS.T3-specific T-cell clones. The DR restriction pattern of each CS.T3-specific T-cell clone was evaluated by comparing the responses to CS.T3 peptide generated in the presence of a panel of HLA-DR homozygous presenting cells (Bell et al., Proc. Natl. Acad. Sci. USA 84, 6234-6238 [1987]). HLA-DR homozygous presenting cells may be obtained from the European Collection for Biomedical Research (E.C.B.R.), European Collection of Human Lymphoblastoid Cell Lines, Istituto Nazionale per la Ricerca sul Cancro, Immunogenetics Lab. Viale Benedetto XV,10, 16132 Genova, Italy. The HLA-DR homozygous presenting cells used to generate the data in Table 1 namely the DR1 homozygous presenting cell EDR, the DR2 homozygous presenting cell NOL, the DR4 homozygous presenting cell BSM, the DR5 homozygous presenting cell ATH, the DRw6 homozygous presenting cell APD, the DR7 homozygous presenting cell EKR and the DR9 homozygous presenting cell DKB were obtained from the Department of Immunohaematology, University Hospital, Leiden, The Netherlands (Drs. E. Goulmy and J. van Rood). The cells were maintained in RPMI 1640 medium (Gibco, Paisley, Scotland) supplemented with 2 mM L-glutamine, 1 mM sodium pyruvate, $5 \times 10^{-5}$ M β-mercaptoethanol, 1% non-essential amino acids (100% stock solution; Gibco), 50 U/ml streptomycin and 10% fetal calf serum. The lines are EPstein-Barr virus-transformed B (EBV-B) cell lines, which were irradiated (5000 Rad) before being used as antigen-presenting cells.

It is emphasized that the DR homozygous presenting cells are not essential to perform the invention. They are used in the present Example only to show that the CS.T3 polypeptide is indeed a universally recognized T-cell epitope.

Definition of CS.T3 determinants recognized by T-cell clones restricted by different DR alleles Because of the wide range of DR types able to present the single CS.T3 peptide it was suspected that the peptide might contain more than one T-cell epitope. To determine if T-cell clones restricted by different DR molecules recognize different determinants on the CS.T3 sequence the proliferative responses of the T-cell clones in the presence of a series of peptides shortened one residue at a time from either the N- or the C-terminus were assayed.

Peptides with the amino acid sequence indicated in Table 2 were synthesized, cleaved and purified by HPLC as described above. These peptides are derivatives of the CS.T3 peptide with 1, 2 or more amino acids deleted at either the N-terminus or the C-terminus. T-cells ($2 \times 10^4$) of the clones shown in Table 1 were cultured with irradiated autologous EBV-B cells ($10^4$) in the presence of various antigen concentrations, ranging from 0.1 to 100 µg/ml. Any peptide that failed to stimulate proliferation at 100 µg/ml was considered to be non-antigenic (-). Peptides giving up to 50% of the maximum values obtained in the presence of the full length peptide (378-398) are indicated as (+) whereas peptides giving values comparable to the full length peptide CS.T3 (378-398) are indicated by (++). Each clone is representative of a group (at least 4) of CS.T3-specific clones with the same DR restriction.

TABLE 2

| PEPTIDE | AMINO ACID SEQUENCE(*) | | DR1 | DR2 | DR4 | DR5 | DRw6 | DR7 | DR9 |
|---|---|---|---|---|---|---|---|---|---|
| 378-398 | DIEKKIAKMEKASSVFNVVNS | (XIII) | ++ | ++ | ++ | ++ | ++ | ++ | ++ |
| 379-398 | IEKKIAKMEKASSVFNVVNS | (VIII) | ++ | +++ | ++ | ++ | ++ | ++ | ++ |
| 380-398 | EKKIAKMEKASSVFNVVNS | (XII) | ++ | ++ | ++ | ++ | ++ | ++ | ++ |
| 381-398 | KKIAKMEKASSVFNVVNS | | + | ++ | ++ | + | ++ | ++ | − |
| 382-398 | KIAKMEKASSVFNVVNS | | − | ++ | ++ | − | − | − | − |
| 383-398 | IAKMEKASSVFNVVNS | | − | ++ | + | − | − | − | + |
| 384-398 | AKMEKASSVFNVVNS | | − | ++ | − | − | − | − | ++ |
| 385-398 | KMEKASSVFNVVNS | | − | + | − | − | − | − | − |
| 386-398 | MEKASSVFNVVNS | | − | − | − | − | − | − | − |
| 378-397 | DIEKKIAKMEKASSVFNVVN | (IV) | ++ | ++ | ++ | ++ | ++ | ++ | ++ |
| 378-396 | DIEKKIAKMEKASSVFNVV | (III) | ++ | ++ | ++ | ++ | ++ | ++ | ++ |
| 378-395 | DIEKKIAKMEKASSVFNV | (II) | ++ | ++ | ++ | ++ | ++ | ++ | + |
| 378-394 | DIEKKIAKMEKASSVFN | | ++ | − | + | ++ | ++ | + | − |
| 378-393 | DIEKKIAKMEKASSVF | | ++ | − | − | ++ | ++ | − | − |
| 378-392 | DIEKKIAKMEKASSV | | ++ | − | − | ++ | + | − | − |
| 378-391 | DIEKKIAKMEKASS | | − | − | − | ++ | − | − | − |
| 378-390 | DIEKKIAKMEKAS | | − | − | − | + | − | − | − |
| 378-389 | DIEKKIAKMEKA | | − | − | − | − | − | − | − |

(*)one letter code of amino acids, see: Hood, Wilson, Wood, "Molecular Biology of Eucaryotic Cells", p. 287, W.A. Benjamin, Inc., Menlo Park, California, U.S.A. [1975]

The peptide 380-398 having the amino acid sequence XII, the peptide 378-395 having the amino acid sequence II and the larger peptides having the amino acid sequences XIII, VIII, IV and III were stimulatory in all the cases examined. However shorter peptides were able to distinguish different recognition patterns for CS.T3-specific clones restricted to different DR molecules. At the two extremes stand DR2- and DR5-restricted clones. Deletions from the C-terminal end until the Val at position 395 and from the N-terminal until $Ala_{384}$ were without appreciable effect for the DR2-restricted clones. Deletion of the $Ala_{384}$ decreased the recognition to <50% at any dose tested. Further removal of $Lys_{385}$ from the N-terminal or $Val_{395}$ from the C-terminus resulted in complete loss of recognition. Conversely DR5-restricted clones could respond until deletion of $Lys_{381}$ from the N-terminal end and deletion of $Ser_{390}$ from the C-terminal end. The minimal regions, as defined by separate N- and C-terminal truncations, which are stimulatory in association with DR2 and DR5 therefore correspond to residues $Lys_{385}$-$Val_{395}$ and $Lys_{381}$-$Ser_{390}$ respectively. Table 2 also shows that the minimal stimulatory region for DR4 is included between residues 383-394, the region for both DRw6 and DR7 corresponds to residues 381-393/394 while DR1-restricted clones recognize either 382-395 (not shown) or 381-392. The responses of DR9 restricted T-cell clones to the truncated peptides deserve further mention. For these clones (4 out of 4 tested) deletion of Lys 381 resulted in loss of recognition, similarly 381-398 peptide was not recognized over a wide range of concentrations. However further removal of Lys 382 and Ile 383 leads to reappearance of immunogenicity. Finally peptide 385-398 was totally non-stimulatory. Taken together the data presented in Table 2 indicate that different overlapping determinants are seen in the context of different DR molecules.

Antibody response in mice immunized by (NANP)3-CS.T3 peptide

The following results show that the dominant site for human T-cells described above can function as a helper determinant for an anti-(NANP)3 response in different mouse strains. The repetitive (NANP)3-sequence coupled to the CS.T3 peptide was administered to 7 different inbred strains and both anti-$NANP_n$ and anti-sporozoite antibody responses were determined.

Mice (2 per group) were immunized at the base of the tail with 50 μg of (NANP)3-CS.T3 in incomplete Freund's adjuvant (IFA). Eight weeks later, they were boosted with 25 μg of the immunogen in complete Freund's adjuvant (CFA). Plasma were taken between 2 and 6 weeks later and were tested individually by ELISA (Rita Togna et al., J. Immunol. 137, 2956-2960 [1986]) for the presence of anti-(NANP)50 antibody. ELISA-titres are geometric means of the last dilution of plasma with $OD_{455} > 0.1$ and >2 times $OD_{455}$ of plasma from mice injected with saline. The antigen used to coat the ELISA plates was (NANP)50.

TABLE 3

| | | Anti-(NANP)50 | | Anti-sporozoite | |
|---|---|---|---|---|---|
| Mouse strain | H-2 | Day 0 | Day 70-98 | Day 0 | Day 70-98 |
| C57BL/6 | b | <150 | 2343 | <40 | 320 |
| BALB/c | d | <150 | 5860 | <10 | >1280 |
| B10.MOla | f | <150 | 938 | <40 | 40 |
| C3H.HeJ | k | <150 | 2343 | <40 | 160 |
| C3H.Q | q | <150 | 3705 | <40 | 320 |
| B10.RIII | r | <150 | 14647 | <40 | >1280 |
| B10.SOla | s | <150 | 1482 | <40 | >1280 |

Table 3 shows that all the different strains tested mounted an antibody response against both (NANP)50 and sporozoites. It was already known that C57BL/6 mice recognized a T-cell site comprising the repetitive region (Good et al., [1986], supra; del Guidice et al., [1986], supra). All the other strains which do not recognize the repetitive region, must have been recognizing the CS.T3 determinant. The fact that all the strains tested respond implies that the CS.T3 T-cell site is recognized in association with many different mouse Ia molecules in addition to the many human MHC gene's products tested and represents therefore a universally recognized T-cell epitope.

Preparation of a multiple antigenic peptide system B cell epitope containing the CS.T3 peptide All optically active amino acids were of the L-configuration and checked for purity by thin-layer chromatography, melting point determination, nuclear magnetic resonance analysis and by determining the optical rotation. $N^\alpha$-Boc amino were used in the synthesis and trifunctional amino acids were protectd as $N^\alpha$-Boc-Lys-(2-ClZ), $N^\alpha$-Boc-AsP(OcHex), $N^\alpha$-Boc-Ser(Bzl) and $N^\alpha$-Boc-Glu(OBzl). Boc-Asn-Ala-Asn-Pro-OBzl was catalytically hydrogenated and the resultant Boc-Asn-Ala-Asn-Pro-OH was shown to be homogeneous by high performance liquid chromatography (HPLC). Solvents and reagents used were of the highest purity. Couplings were performed by the DCC in situ or symmetrical anhydride procedures exept for asparagine which was coupled as the hydroxybenzotriazole ester. The peptides were prepared by the Merrifield solid phase procedure with sequential coupling of amino acids using the Applied Biosystems Peptide Synthesizer Model 430A (Applied Biosystems, Foster City, Calif., U.S.A.) or by a manual procedure.

Preparation of Boc-Cys(Dmb)-Benzhydrylamine-resin, 1

A suspension of benzhydrylamine resin (24 g, 0.54 meq/g, 12.96 mmol) was placed in a reaction vessel clamped to a manual shaker and successively washed with methylene chloride ($CH_2Cl_2$; 4×250 ml), 10% diisopropylethylamine (DIEA; 1×250 ml, 10 min) and $CH_2Cl_2$ (1×250 ml). The procedure was repeated, and the resin was then washed with methanol (MeOH; 2×250 ml), $CH_2Cl_2$ (2×250 ml) and dimethylformamide (DMF; 4×250 ml). A solution of Boc-Cys(Dmb)-OH (13.27 g, 38.9 mmol) in DMF (200 ml) was added and shaken for 5 min. To the slurry was then added a solution of benzotriazol-1-yloxy-tris(dimethylamino)-phosphonium hexafluorophosphate (BOP; 17.20 g, 38.9 mmol) in DMF (50 ml) followed immediately by the addition of DIEA (20.32 ml, 116.6 mmol) and shaking continued for 150 minutes. An aliquot of resin was removed (100 mg) and assayed by the Gisin test (Anal. Chim. Acta 58, 248-249 [1972]). The substitution was found to be 0.23 meq/g-resin. The total resin was filtered, washed with DMF (2×250 ml), $CH_2Cl_2$ (2×250 ml) and recoupled with Boc-Cys(Dmb) (13.27 g, 38.9 mmol) and 1,3-dicyclohexylcarbodiimide (DCC; 8.02 g, 38.2 mmol) in $CH_2Cl_2$ (250 ml) for 24 hours. The Gisin test was repeated on a 100 mg resin aliquot and the loading determined to be 0.36 mmol/g-resin. The resin was suspended in 150 ml of pyridine and 150 ml acetic anhydride, shaken for 1 hour, filtered and washed with $CH_2Cl_2$ (2×250 ml), MeOH (2×250 ml), $CH_2Cl_2$ (2×250 ml) and dried in vacuo.

Preparation of Boc-Aca-Cys(Dmb)-benzhydrylamine-resin, 2

Boc-Cys(Dmb)-benzhydrylamine-resin, 1, (20 g. 7.2 mmol) was washed with $CH_2Cl_2$ (250 ml), deprotected with 250 ml of 50% TFA-$CH_2Cl_2$ for 1 min. washed with $CH_2Cl_2$ (250 ml) and deprotected again with 250 ml of 50% TFA-$CH_2Cl_2$ for 20 min. The resin was then washed with $CH_2Cl_2$ (3×250 ml), MeOH (2×250 ml) and $CH_2Cl_2$ (2×250 ml). Neutralization was carried out by washing with 10% DIEA-$CH_2Cl_2$ (2×250 ml) 5 minutes each, $CH_2Cl_2$ (2×250 ml), MeOH (2×250 ml) and $CH_2Cl_2$ (4×250 ml). A solution of Boc-amino caproic acid (Boc-Aca-OH) (0.66 g, 2.88 mmol, 0.40 eq) in $CH_2Cl_2$ (250 ml) was then added and the reaction mixture agitated for 5 minutes. Dicyclohexylcarbodiimide (0.59 g, 2.88 mmol, 0.40 eq) was added and the mixture agitated for 2 h. The mixture was filtered and washed with $CH_2Cl_2$ (2×100 ml), MeOH (2×100 ml) and $CH_2Cl_2$ (2×100 ml). An aliquot of resin (50.3 mg) was hydrolyzed (6M HCl/propionic acid, 110° C. 24 hours) and amino acid analysis showed a substitution of 0.08 mmol of Aca per gram-resin. The resin was "capped" with $Ac_2O$-pyridine as for compound 1.

Preparation of $(Lys)_7$-Aca-Cys(Dmb)-Benzhydrylamine-resin, 3

Boc-Aca-Cys(Dmb)-benzhydrylamine-resin, 2, (20 g, 0.08 meq/g, 1.6 mmol) was subjected to the washings, deprotection and neutralization procedure specified for compound 1. Boc-Lys(Boc)-OH (1.99 g, 5.76 mmol, 3.6 eq) was dissolved in $CH_2Cl_2$ (250 ml) and added to the H-Aca-Cys(Dmb)-BHA-resin, 2 and subjected to a cycle of solid phase synthesis (2 hours) using DCC (1.18 g, 5.76 mmol, 3.6 eq) as the condensing reagent. An aliquot of Boc-Lys(Boc)-Aca-Cys(Dmb)-BHA-resin, 3a, (100 mg) was hydrolyzed and indicated a substitution of 0.056 meq Lys/g resin. Solid phase peptide synthesis was continued using Boc-Lys(Boc)-OH (3.98 g, 11.52 mmol, 3.6 eq) and DCC (2.36 g, 11.52 mmol, 3.6 eq) by the above procedure. Amino acid analysis of the peptide resin indicated a loading at 0.15 meq Lys/g of $(Lys)_3$-Aca-Cys(Dmb)-BHA-resin, 3b. Synthesis was continued using Boc-Lys(Boc)-OH (7.96 g 23.04 mmol, 3.6 eq) and DCC (4.75 g, 23.04 mmol, 3.6 eq).by the above procedure. An aliquot of peptide resin was hydrolyzed and the amino acid composition indicated 0.20 meq Lys/g substitution of $(Lys)_7$-Aca-Cys(Dmb)-BHA-resin, 3c. The peptide resin was dried in vacuo. Final weight=20.1 g.

Preparation of $[(Asn-Ala-Asn-Pro)_3]_8$-$Lys_7$-Aca-Cys-($NH_2$), 4

A portion (5.0 g, 0.20 meq Lys/g, 1.0 meq Lys, 0.143 mmol peptide) of $Lys_7$-Aca-Cys-(Dmb)-BHA-resin 3c, was subjected to a cycle of solid phase peptide synthesis using the protected tetrapeptide, Boc-Asn-Ala-Asn-Pro-OH, (1.28 g, 2.5 mmol, 2.5 eq), and BOP reagent (1.1 g, 2.5 mmol, 2.5 eq) in DMF (250 ml containing 0.5% of DIEA). After 18 hours, the ninhydrin test indicated that the reaction was complete. An aliquot of the peptide-resin was hydrolyzed (6N HCl, 150° C. 2 hours) and gave the expected amino acid composition: AsP, 15.90 (16); Pro, 6.99 (8); Ala, 8.50 (8); Lys, 7.00 (7). The resin was deprotected with TFA and the above procedure was repeated with a second cycle using Boc-Asn-Ala-Asn-Pro—OH (single coupling), the resin hydrolyzed and the amino acid composition showed the expected incorporation: Asp, 32.42 (32); Pro, 15.07 (16); Ala 16.92 (16); Lys, 7.26 (7). After deprotection with TFA a final coupling, as above with Boc-Asn-Ala-Asn-Pro—OH, gave 6.3 g of $[(Boc-Asn-Ala-Asn-Pro)_3]_8$-$Lys_7$-Aca-Cys-BHA-resin. Hydrolysis of an aliquot (as above) gave: AsP, 48.00 (48); Pro, 20.32 (24); Ala, 24.96 (24); Lys, 7.26 (7). A portion of this material (6 g) was cleaved with anhydrous hydrofluoric acid (HF; 60 ml containing 10% 1-propanethiol) at 0° C. for two hours. The HF was evaporated at 0° C. (high vac, CaO trap) and the crude peptide and resin mixture triturated with EtOAc, extracted with TFA (3×50 ml), evaporated, triturated with anhydrous ether and dried to give 1.3 g of crude peptide.

The crude peptide (1.3 g) was dissolved (40 ml of 0.025% TFA/$H_2O$), filtered (0.45μ Millex-HV filter) and loaded onto a Nucleosil C-18 column (1×50 cm). The column was eluted (7 ml/min) with a solvent system consisting of A: $H_2O$ (containing 0.025% TFA) and B: $CH_3CN$ (containing 0.025% TFA) in a linear gradient mode from 10% (B) to 25% (B) in 2 h. Fractions were collected (7 ml) and aliquots analyzed by analytical HPLC (Column: Lichrosorb RP-8 (5μ); Eluant: (A) 0.1M HClO$_4$ (pH 2.5) (B) CH$_3$CN; Gradient: 15% B to 55% B in 20 min; Flow rate: 1 ml/min; Retention time: 9.1 min.) The product emerged in fractions (10–18) which were combined, evaporated and lyophilized to give pure [(NANP)$_3$]$_8$-K$_7$-Aca-Cys-NH$_2$, 4. Yield: 1.06 g (67.3%). The compound was shown to be homogeneous by analytical HPLC and gave the expected amino acid composition after acid hydrolysis (6N HCl; 150° C.; 1 hour): AsP, 45.5 (48); Pro, 23.8 (24); Ala, 23.6 (24); Lys, 7.0 (7); Cys, 1.12 (Ellman test; see Ellman, Arch. Biochem. Biophys. 82 70–77 [1959]). Further confirmation of structure was provided by microsequence analysis and FAB mass spectroscopy: Calculated (M+2H)$^2$; 10,644,5; Found: 10,642.

Preparation of [Ala$^{384,389}$]-P.falciparum CS(378–398)—NH$_2$, 5a

Boc-Ser(Dmb)-BHA-resin (3.4 g, 0.35 meq/g-resin. 1.19 mmol) was charged into a 100 ml reaction vessel clamped on a manual shaker and peptide synthesis performed for a total of 4 cycles to give P.falcioarum CS(394–398)-BHA-resin (3.5 g). A 1.5 g (0.5 mmol) portion was removed and subjected to the additional 25 cycles of solid phase synthesis using the Applied Biosystems 430A synthesizer to yield 2.2 g of protected [Ala$^{384,389}$]-P.falciparum CS(378–398)-BHA-resin. A 0.4 g portion of the protected peptide resin was cleaved with anhydrous HF (as for compound 4) and 0.226 g of crude [Ala$^{384,389}$]-P.falciparum CS(378–398)—NH$_2$ was obtained. The crude material was dissolved in 10 ml of H$_2$O, filtered (0.45 μ type HA Millipore filter) and loaded onto a Waters C-18 column (1.9×30 cm) available from Wates Associates, Milford, Mass., U.S.A. The column was eluted (8 ml/min) with a solvent system consisting of (A) water (containing 0.025% TFA) and (B) CH$_3$CN (containing 0.025% TFA) in a linear gradient mode from 10% (B)–35% (B) in 120 minutes. Fractions were collected (every minute) and aliquots analyzed by analytical HPLC (Column: Lichrosorb RP-8 (10 μ); Eluant: (A) 0.1M HClO$_4$ (pH 2.5) (B) CH$_3$CN; Gradient: 20% B to 40% B in 20 min; Flow rate: 1.5 ml/min; Retention time: 16 minutes). The product emerged in fractions 68 and 69 which were combined, evaporated and lyophilized to give 10 mg (3.7% yield) of pure [Ala$^{384,389}$]-P.falciparum CS(378–398)—NH$_2$, 5a which is the amidated form of the CS.T3 peptide. The product was shown to be homogeneous by analytical HPLC and gave the correct amino acid composition after acid hydrolysis (6N HCl; 150° C.; 24 hours): Asp, 2.83 (3); Ser. 2.79 (3); Met, 0.90 (1); Glu, 1.89 (2); Ala, 2.00 (2); (6N HCl; 110° C.; 72 hours): Val, 2.89 (3); Ile, 1.87 (2); Phe, 0.97 (1); Lys, 4.14 (4). Further confirmation of structure was provided by FAB mass spectroscopy. Calculated (M+H)$^+$: 2337.7, Found: 2338.0.

Preparation of Ac-Cys-Aca[Ala$^{384,389}$]-P.falciparum CS(378–398)—NH$_2$, 5b

A 0.8 g portion (0.182 mmol) of protected [Ala$^{384,389}$]-P.falciparum CS(378–398)-BHA-resin (see above) was subjected to 2 cycles of solid phase synthesis and acetylated (50% Ac$_2$O/pyridine; 30 ml; 1 hour) to give the protected Ac-Cys-Aca[Ala$^{384,389}$]-P.falciparum CS(378–398)-BHA-resin (600 mg). Treatment with anhydrous HF (as for compound 4) yielded 360 mg of crude product which was dissolved in water, filtered (as in example 5a) and applied onto a μ-Bondapak C-18 column (1.9×30 cm). The column was eluted (10 ml/minute) with a solvent system consisting of (A) H$_2$O (containing 0.025% TFA) and (B) CH$_3$CN (containing 0.025% TFA) in a linear gradient mode from 20% (B)–40% (B) in 90 minutes. Fractions were collected (every minute) and aliquots analyzed by analytical HPLC (Column: Lichrosorb RP-8 (5μ); Eluant: (A) 0.1M HClO$_4$ (pH 2.5) (B) CH$_3$CN; Gradient: 30% B to 55% B in 20 minutes; Flow rate: 1 ml/minute; Retention time: 10 minutes). The product emerged in fractions 33–35 which were combined, evaporated and lyophilized. Yield: 19 mg (3.4% yield). The purified Ac-Cys-Aca[Ala$^{384,389}$]-P.falciparum CS(378–398)—NH$_2$,5b, was shown to be essentially homogeneous by analytical HPLC and gave the expected amino acid composition (6N HCl; 110° C.; 24 hours): Asp, 2.87 (3); Ser, 2.77 (3); Glu, 1.98 (2); Ala, 2.00 (2); Val, 2.05 (2); Ile, 1.69 (2); Met, 0.99 (1); Phe, 1.00 (1); Lys, 4.07 (4); Cys, 0.86 (Ellman Test). Further confirmation of structure was provided by FAB mass spectroscopy. Calculated. (M+H)$^+$: 2596.2; Found: 2595.8.

Synthesis of [(NANP)$_3$]$_8$

```
                ┌─────────────┐
K₇Aca—Cys— NH₂  Ac—Cys—
```

-Aca[Ala$^{384,389}$]-P.falciparum CS(378–398)—NH$_2$, 6

Ac-Cys-Aca[Ala$^{384,389}$]-P.falciparum CS(378–398)—NH$_2$, 5b, (2.5 mg; 0.82 μmol, 2 eq) and [(Asn-Ala-Asn-Pro)$_3$]$_8$Lys$_7$-Aca-Cys—NH$_2$, 4, (4.74 mg; 0.41 μmol; 1 eq) were dissolved in 1.8 ml of distilled water followed by an addition of 7.6 ml of 0.2M NH$_4$HCO$_3$ (pH 7.8). The reaction mixture was left standing at room temperature for 24 hours and lyophilized. The residue was dissolved in 2 ml of 0.025% TFA/H$_2$O, filtered and applied onto a Nucleosil C-18 column (0.4×25 cm). The column was eluted (1.5 ml/minute) with a solvent system consisting of (A) water (containing 0.025% TFA) and (B) CH$_3$CN (containing 0.025% TFA) in a linear gradient mode from 10% (B)–40% (B) in 120 minutes. Fractions were collected (every minute) and aliquots analyzed by analytical HPLC (Column: RP-8 (5μ); Eluent: (A) 0.1M HClO$_4$ (pH 2.5) (B) CH$_3$CN; Gradient: 10% B to 55% B in 30 minutes; Flow rate: 1 ml/minute; Retention time: 21 minutes). The product emerged in fractions 42–45 which were combined, evaporated and lyophilized to give 1.5 mg (25% yield) of product, 6. The product was shown to be homogeneous by analytical HPLC and gave the expected amino acid composition after acid hydrolysis (6N HCl; 110° C.; 24 hours): Asp, 52.0 (51); Ser, 3.4 (3); Glu, 2.5 (2); Ala, 24.7 (26); Val, 2.5 (3); Met, 1.0 (1); Ile, 2.2 (2); Phe, 1.1 (1); Lys, 11.5 (11).

Preparation of [Ala$^{384,389}$]-P.falciparum CS(380–396)—NH$_2$, 7a

Boc-Val-benzhydrylamine-resin (1.5 g, 0.2 meq/g; 0.3 mmol) was subjected to 16 cycles of solid phase peptide synthesis using the Applied Biosystems 430A synthesizer to yield 2.1 g of protected [Ala$^{384,389}$]-P.falciparum CS(380–396)-BHA-resin. A 0.4 g portion of the protected peptide resin was cleaved with anhydrous HF (as for compound 4) and 121 mg of crude [Ala$^{384,389}$]-P.falciparum CS(380–396)—NH$_2$, was obtained. A portion of the crude product (60 mg) was dissolved in 0.025% TFA/H$_2$O, filtered and applied onto a Nucleosil C-18 column (1.0×50 cm). The column was eluted (2.5 ml/minute) with a solvent system consisting of (A) water (containing 0.025% TFA) and (B) CH₃CN (containing 0.025% TFA) in a linear gradient mode from 15% (B)-35% (B) in 180 minutes. Fractions were collected (every minute) and aliquots analyzed by analytical HPLC (Column: Lichrosorb RP-8 (5μ); Eluant: (A) 0.1M HClO₄ (pH 2.5) CH₃CN; Gradient: 30% B to 55% B in 20 minutes; Flow rate: 1.0 ml/minute; Retention time: 8.0 minutes). The product emerged in fractions 34-46 which were combined evaporated and lyophilized to give 14 mg (20% yield) of pure [Ala$^{384,396}$]-P.falciparum CS(380-396)—NH₂, 7a. The product was shown to be homogeneous by analytical HPLC and gave the correct amino acid composition after acid hydrolysis (6N HCl; 150° C.; 1 hour): AsP, 0.95 (1); Ser, 1.88 (2); Glu. 2.00 (2); Ala, 2.00 (2); Met, 0.93 (1); (6N HCl; 110°; 72 hours): Val, 2.91 (3); Ile, 0.97 (1); Phe, 1.17 (1); Lys, 4.10 (4). Further confirmation of structure was provided by microsequence analysis and FAB mass spectroscopy. Calculated (M+H)⁺: 1908.3; Found: 1908.0.

Preparation of Ac-Cys-Aca-[Ala$^{384,389}$]-P.falciparum CS(380-396)—NH₂, 7b

Boc-Val-benzhydrylamine-resin, prepared as in compound 1 (20 g; 0.5 mmol/g; 10 mmol) was charged onto a 1 liter reaction vessel, clamped on a Kraft Shaker and solid phase peptide synthesis performed for a total of 19 cycles to give Ac-Cys-Aca[Ala$^{384,389}$]-P.falciparum CS(380-396)-BHA-resin (44.9 g). A portion of the protected peptide resin (5 g; 1.11 mmol) was treated with anhydrous HF (as for compound 4) and 2.21 g of crude product obtained A portion (1.1 g) of the crude product was dissolved in 40 ml of 0.025% TFA/H₂O, filtered and applied onto a Nucleosil C-18 column (2.2×25 cm). The column was eluted (9 ml/min) with a solvent system consisting of (A) H₂O (containing 0.025% TFA) and (B) CH₃N (containing 0.025% TFA) in a linear gradient mode from 10% (B)-35% (B) in 120 minutes. Fractions were collected (every minute) and aliquots analyzed by analytical HPLC (Column: Lichrosorb RP-8 (5μ); Eluant: (A) 0.1M HClO₄ (pH 2.5) (B) CH₃CN; Gradient: 30% B to 55% B in 20 minutes; Flow rate: 1.0 ml/minute; Retention time: 10 minutes). The product emerged in fractions 65-72 which were combined, evaporated and lyophilized to give 144 mg (9.9% yield) of product. The purified Ac-Cys-Aca-[Ala$^{384-389}$]-P.falciparum CS(380-396)—NH₂, 7b, was shown to be homogeneous by analytical HPLC and gave the expected amino acid composition after acid hydrolysis (6N HCl; 150° C.; 1 hour): AsP, 1.09 (1); Ser, 1.90 (2); Glu, 1.98 (2); Ala, 2.00 (2); Met, 0.93 (1); Phe, 0.95 (1). (6N HCl; 110° C.; 72 hours): Val, 2.76 (3); Ile, 1.04 (1); Lys, 4.35 (4); Cys, 1.10 (Ellman Test). Further confirmation of structure was provided by FAB mass spectroscopy. Calculated (M+H)$^{30}$: 2166.6; Found: 2167.0.

Preparation of Ac-Cys(S-pyridyl)-Aca[Ala$^{384,389}$]-P.falciparum CS(380-396)—NH₂, 8

2,2'-Dipyridyl disulfide (10.8 mg, 49 μmol, 1.64 eq) was dissolved in trifluoroethanol (14 ml, containing 4% AcOH) and added to a stirring solution of Ac-Cys-Aca-[Ala$^{384,289}$]-P.falciparum CS(380-396)—NH₂, 7b, (78 mg, 29.8 μmol, 1 eq) in trifluoroethanol (14 ml. containing 4% AcOH). The solution was stirred for 1 hour, evaporated and the residue triturated with anhydrous ether and dried. Yield: 73.3 mg (93.9% yield). The product was shown to be essentially homogeneous by analytical HPLC (Column; Nucleosil C-18 (5μ); Eluant: (A) H₂O (containing 0.025% TFA), (B) CH₃CN (containing 0.025% TFA); Gradient: 15% B to 40% B in 20 minutes and held at 40% B for 15 minutes; Flow rate: 1.4 ml/minute; Retention time: 23 minutes). Amino acid analysis after acid hydrolysis (6N HCl; 110° ; 72 hours) gave the expected composition: AsP, 1.07; Ser, 2.05; Glu, 2.13; Ala, 2.03; Val. 1.87; Met, 0.94; Ile, 0.92; Phe, 0.92; Lys, 3.94; Aca, 0.98. Ellman Test revealed the absence of the cysteinyl sulfhydryl group. ¹H-NMR (DMSO-d₆) was compatible with the structure and showed the presence of the pyridyl moiety: δ 7.22 (1H, d), δ 7.32 (2H, m) and δ 7.83 (1H, m). U.V. λ max (50% TFE/H₂O) 280 nm (ε 3780).

Preparation of [(Asn-Ala-Asn-Pro)₃]₈-Lys₇-Aca $$\overline{Cys—NH_2\ Ac—Cys—Aca[Ala^{384.389}]}$$

-P.falciparum CS(380-396)—NH₂, 9

Ac-Cys(S-pyridyl)-Aca[Ala$^{384,389}$]-P.falciparum CS(380-396)—NH₂, 8, (53.4 mg, 20.4 μmol, 2.35 eq) was dissolved in trifluoroethanol (4.8 ml) and 0.2 M NH₄HCO₃ (12 ml, PH 8.7) was added. To the stirring solution was added [(Asn-Ala-Asn-Pro)₃]₈-Lys₇-Aca-Cys—NH₂, 4 (100.4 mg, 8.69 μmol, 1 eq) in distilled H₂O (7.2 ml) and the reaction mixture stirred for 2 hours at 25° and lyophilized. The residue was dissolved in 10 ml of 0.025% TFA/H₂O, filtered and applied onto a Nucleosil C-18 column (2.2×25 cm). The column was eluted (9 ml/min) with a solvent system consisting of (A) H₂O (containing 0.025% TFA) and (B) CH₃CN (containing 0.025% TFA) in a linear gradient mode from 10% (B)-40% (B) in 100 minutes. Fractions were collected (every minute) and aliquots analyzed by HPLC (Column: Lichrosorb RP-8 (5 μ); Eluant: (A) 0.1M HClO₄ (pH 2.5) (B) CH₃CN; Gradient: 10% B to 55% B in 30 minutes; Flow rate: 1 ml/minute; Retention time: 19.7 minutes). The product emerged in fractions 36-44 which were pooled, evaporated and lyophilized to give 92 mg (74.5% yield) of product. The product was shown to be homogeneous by analytical HPLC and gave the expected amino acid composition after acid hydrolysis (6N HCl; 110° C.; 72 hours): Asp, 51.30 (49); Ser, 1.99 (2); Glu, 2.07 (2); Pro, 25.13 (24); Ala, 26.00 (26); Val, 2.40 (3); Met, 0.96 (1); Ile, 1.04 (1); Phe, 1.03 (1); Lys, 11.35 (11). Ellman Test confirmed the absence of the cysteine SH group. In addition, treatment under reducing conditions with dithiothreitol yielded the starting materials [(Asn-Ala-Asn-Pro)₃]₈-Lys₇-Aca-Cys—NH₂, 4, and Ac-Cys-Aca-[Ala$^{384,389}$]-P.falciparum CS(380-396)—NH₂, 7b. which were confirmed by analytical HPLC.

Antibody response in mice immunized by (MAP-NANP)-CS.T3

BALB/c mice (five per group) were immunized intraperitoneally with 40 μg of (NANP)₃-CS.T3 (□—□) or the compound 6 comprising the amidated form of the polypeptide having the amino acid sequence XIII (the CS.T3 peptide) covalently linked to the MAPS B-cell epitope [(NANP)₃]₈-Lys₇-Aca-Cys—NH₂(♦—♦)in complete Freund's adjuvant (CFA). A boos injection (40 μg of the immunogen in CFA) was given 4 weeks later. Plasma were taken every week as indicated in the FIGURE and tested by enzyme-linked immunoadsorbent assay for the presence of anti-(NANP)$_{50}$ antibody (FIG. 5) and by indirect immunofluorescence for antibodies to sporozoites (FIG. 6) using standard procedures. The titers of antisera raised by compound 6 were 4 times higher compared with those induced by (NANP)$_3$-CS.T3, as measured by indirect immunofluorescence on fixed sporozoites, thus indicating that the combination of the polypeptide representing a universal T-cell epitope with the MAPS B-cell epitope mentioned above leads to a stronger immune response than when the B-cell epitope is the linear peptide (NANP)$_3$.

I claim:

1. An antigenic structure comprised of a polypeptide of the amino acid sequence $$R^1\text{—Glu—Lys—Lys—Ile—Ala—Lys—Met—Glu—Lys—Ala—Ser—Ser—Val—Phe—Asn—Val—}R^2 \quad (I)$$

wherein $R^1$ is H-Asp-Ile-, H-Ile- or H- and $R^2$ is -Val-Asn-Ser—OH, -Val-Asn—OH, -Val—OH or —OH and a B-cell epitope.

2. The antigenic structure of claim 1 wherein the B-cell epitope is a multiple antigenic peptide.

3. The antigenic structure of claim 2 wherein the multiple antigenic peptide comprises multimers of the repeat sequence NANP present in the circumsporozoite protein of Plasmodium falciparum.

4. The antigenic structure of claim 3 having the formula

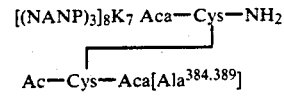

P.falciparum CS(378-398)—NH$_2$.

5. The antigenic structure of claim 3 having the formula

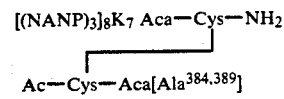

P.falciparum CS(380-396)—NH$_2$.

6. An immunogenic composition comprising an antigenic structure containing a polypeptide of the amino acid sequence:

$$R^1\text{—Glu—Lys—Lys—Ile—Ala—Lys—Met—Glu—Lys—Ala—Ser—Ser—Val—Phe—Asn—Val—}R^2 \quad (I)$$

wherein $R^1$ is H-Asp-Ile-, H-Ile- or H- and $R^2$ is -Val-Asn-Ser—OH, -Val-Asn—OH, -Val—OH or —OH and a B-cell epitope and a pharmaceutically acceptable adjuvant.

7. The composition of claim 6 wherein the polypeptide is selected from the group consisting of:

H—Asp—Ile—Glu—Lys—Lys—Ile—Ala—Lys—Met—Glu—Lys—Ala—Ser—Ser—Val—Phe—Asn—Val—OH   (II),

H—Asp—Ile—Glu—Lys—Lys—Ile—Ala—Lys—Met—Glu—Lys—Ala—Ser—Ser—Val—Phe—Asn—Val—Val—OH   (III),

H—Asp—Ile—Glu—Lys—Lys—Ile—Ala—Lys—Met—Glu—Lys—Ala—Ser—Ser—Val—Phe—Asn—Val—Val—Asn—OH   (IV),

H—Ile—Glu—Lys—Lys—Ile—Ala—Lys—Met—Glu—Lys—Ala—Ser—Ser—Val—Phe—Asn—Val—OH   (V),

H—Ile—Glu—Lys—Lys—Ile—Ala—Lys—Met—Glu—Lys—Ala—Ser—Ser—Val—Phe—Asn—Val—Val—OH   (VI),

H—Ile—Glu—Lys—Lys—Ile—Ala—Lys—Met—Glu—Lys—Ala—Ser—Ser—Val—Phe—Asn—Val—Val—Asn—OH   (VII),

H—Ile—Glu—Lys—Lys—Ile—Ala—Lys—Met—Glu—Lys—Ala—Ser—Ser—Val—Phe—Asn—Val—Val—Asn—Ser—OH   (VIII),

H—Glu—Lys—Lys—Ile—Ala—Lys—Met—Glu—Lys—Ala—Ser—Ser—Val—Phe—Asn—Val—OH   (IX),

H—Glu—Lys—Lys—Ile—Ala—Lys—Met—Glu—Lys—Ala—Ser—Ser—Val—Phe—Asn—Val—Val—OH   (X),

H—Glu—Lys—Lys—Ile—Ala—Lys—Met—Glu—Lys—Ala—Ser—Ser—Val—Phe—Asn—Val—Val—Asn—OH   (XI),

H—Glu—Lys—Lys—Ile—Ala—Lys—Met—Glu—Lys—Ala—Ser—Ser—Val—Phe—Asn—Val—Val—Asn—Ser—OH   (XII), or

H—Asp—Ile—Glu—Lys—Lys—Ile—Ala—Lys—Met—Glu—Lys—Ala—Ser—Ser—Val—Phe—Asn—Val—Val—Asn—Ser—OH   (XIII),

* * * * *